United States Patent [19]

Chang et al.

[11] Patent Number: 5,016,018

[45] Date of Patent: May 14, 1991

[54] APERTURE SYNTHESIZED RADIOMETER USING DIGITAL BEAMFORMING TECHNIQUES

[75] Inventors: Donald C. D. Chang, Thousand Oaks; Edwin A. Kelley, Los Angeles, both of Calif.

[73] Assignee: Hughes Aircraft Company, Los Angeles, Calif.

[21] Appl. No.: 326,935

[22] Filed: Mar. 22, 1989

[51] Int. Cl.⁵ .............................................. G01S 7/00
[52] U.S. Cl. .................................... 342/351; 342/195
[58] Field of Search ............... 342/351, 372, 375, 377, 342/195, 196, 156–157, 755

[56] References Cited

U.S. PATENT DOCUMENTS

| | | | |
|---|---|---|---|
| 3,942,177 | 3/1976 | Danzer et al. | 342/351 |
| 4,630,051 | 12/1986 | Adams et al. | 342/156 X |
| 4,654,666 | 3/1987 | Wiley | 342/351 |
| 4,724,439 | 2/1988 | Wiley et al. | 342/351 |
| 4,814,772 | 3/1989 | Wiley et al. | 342/351 |
| 4,825,215 | 4/1989 | Wiley | 342/351 |
| 4,864,308 | 9/1989 | Raab et al. | 342/351 |
| 4,864,309 | 9/1989 | Wiley et al. | 342/351 |

*Primary Examiner*—Thomas H. Tarcza
*Assistant Examiner*—Tod Swann
*Attorney, Agent, or Firm*—Steven M. Mitchell; Robert A. Westerlund; Wanda K. Denson-Low

[57] ABSTRACT

A digital aperture synthesized radiometer for synthesizing the imaging an image scene. A plurality of antenna arrays receive radiation emitted or reflected from an scene, and an analog to digital coverter converts received radiation into digitized signals. A digital beamformer synthesizes the digitized signals to provide an image corresponding to the scene. The digital beamformer comprises individual digital beamformers which generate a set of fanbeam signals for each array. The beamformers provide for cross track imaging of the scene. A digital interferometer correlates corresponding pairs of fanbeam signals from the two sets of fanbeam signals to produce a chirp signal for each pair. A matched filter processes the chirp signals to transform each chirp signal into a corresponding image point of the scene. This provides for along track imaging of the scene. The beamformers include an amplitude weighting and data turning circuit to reduce fanbeam signal sidelobe levels and eliminate alternate mainlobes from the digitized radiation signals to reduce mainlobe widening. A fast Fourier transform circuit in the beamformers generally comprises a decimation-in-time algorithm implemented by means of a plurality of parallel and cascaded butterfly computation circuits. Image processing methods for achieving digital radiometry are also disclosed.

27 Claims, 5 Drawing Sheets

APERTURE SYNTHESIZED RADIOMETER USING DIGITAL BEAMFORMING TECHNIQUES

BACKGROUND OF THE INVENTION

The present invention relates generally to digital aperture synthesized radiometers, and more particularly to an aperture synthesized radiometer employing digital beamforming including interferometry and which is capable of imaging microwave energy emitted or reflected by earth surface features.

Microwave radiometers are passive remote sensors which can be designed to detect, measure and display the microwave energy emitted by earth surface features and the atmosphere. Such systems, operating at L-band, can be used for soil moisture measurements from a space platform orbiting the earth.

In order to remotely measure soil moisture, three primary steps are involved. These include identifying moisture within the field of view of the measuring system's sensors, measuring the detected moisture level, and displaying the measured levels. Substantially all objects in the natural environment emit electromagnetic energy in the microwave region. The amount of energy emitted by an object is related to its physical temperature and surface emissivity, and it normally varies with frequency.

Moist soil naturally radiates over a large bandwidth in the microwave region, including L-band. Therefore, to measure the moisture content of soil, it is advantageous to tune the remote sensor to the L-band frequency region. Once the soil moisture is identified and measured, it must be imaged. This is done by constructing a ground map of the soil moisture levels. In order to do this, two dimensional ground resolution is required.

One way to achieve soil moisture imaging is to employ a system described in U.S. Pat. No. 4,724,439, entitled "Microwave Radiometer Using Fanbeam Inversion," issued to Carl Wiley and Charles Edlesohn, and assigned to the assignee of the present invention. In this patent, a microwave radiometer is disclosed which reconstructs images using fanbeam inversion. A scanning radiometer utilizes a fanbeam antenna which is mechanically scanned across the scene so that the antenna output is a projection of the scene taken along the direction of the scan. The scanning motion is provided for by a motor coupled to the antenna and controlled by a computer. An inverse Radon transform is employed in the computer to reconstruct the scene.

However, although the above scanning radiometer system performs admirably, the development of digital computers and signal processors provides a means to accomplish the microwave imaging without the use of moving parts or motors, or the like.

SUMMARY OF THE INVENTION

The present invention is an alternative to the above-described scanning radiometer system, and it provides for an aperture synthesized radiometer comprising a plurality of substantially parallel antenna arrays for receiving radiation emitted or reflected from an scene, and an analog to digital converter coupled to the plurality of antenna arrays for converting received radiation into corresponding digitized signals. A digital imaging processor is coupled to the analog to digital converter for processing and synthesizing the digitized dignals to synthesize a large aperture antenna array which provides an image corresponding to the scene.

The digital imaging processor comprises individual digital beamformers coupled to each of the antenna arrays for generating a set of fanbeam signals for each antenna array. The beamformers provide for cross track imaging of the scene. A digital correlating interferometer is coupled to the individual beamformers for converting the sets of fanbeam signals into spot beam images.

The digital interferometer correlates corresponding pairs of fanbeam signals from the two sets of fanbeam signals to produce a slowly varying chirp signal from the images of a given spot on the earth's surface as a space platform on which the radiometer is disposed moves relative to the earth's surface. This provides for along track imaging of the scene. A matched filter is used to transform the slowly varying chirp signals from the output of the digital interferometer into corresponding image points of the scene within each fanbeam.

The individual digital beamformers further comprise an amplitude weighting circuit which provides for amplitude weighting of the digitized radiation signals to reduce fanbeam signal sidelobe levels. Also, a data turning circuit is coupled to the amplitude weighting circuit to eliminate alternate mainlobes from the digitized signals. This reduces mainlobe widening of the digitized signals.

The individual digital beamformers each comprise a fast Fourier transform circuit which transforms the digitized signals into the fanbeam signals. The fast Fourier transform circuit generally comprises a decimation-in-time algorithm implemented by means of a plurality of parallel and cascaded butterfly computation circuits.

By employing the digital beamformers which simultaneously generate multiple fanbeams to provide cross track resolution, and the interferometer and matched filter to provide along track resolution, and hence to produce pixel data for the scene, the present invention provides for a digital aperture synthesized radiometer that achieves remote sensing and imaging of microwave energy.

The present invention also comprises a method of digitally processing an image. The method comprises the steps of receiving radiation emitted or reflected from an scene. This is done by means of a plurality of substantially parallel antenna arrays. The next step involves converting received radiation into corresponding digitized signals. This is accomplished by means of an analog to digital converter coupled to the plurality of antenna arrays. Finally the method provides for processing and synthesizing the digitized signals to provide an image corresponding to the scene. This is achieved by means of a digital imaging processor coupled to the analog to digital converter.

The synthesizing step generally comprises processing and synthesizing the digitized signals which is performed by means of individual digital beamformers coupled to two antenna arrays, and generating a set of fanbeam signals for each antenna array utilizing fast Fourier transforms. This step provides for cross track imaging of the scene. Pairs of fanbeam signals from the beamformers are then correlated. This step is performed by means of a digital interferometer coupled to the individual beamformers.

Because of the motion of the present invention relative to the scene, this process step generates a slowly varying chirp signal for each pair of fanbeam signals for a point source image within the fanbeam. The chirp signals are then processed by means of matched filter coupled to the digital interferometer to transform each chirp signal into a corresponding point image intensity in the scene.

BRIEF DESCRIPTION OF THE DRAWING

The various features and advantages of the present invention may be more readily understood with reference to the following detailed description taken in conjunction with the accompanying drawing, wherein like reference numerals designate like structural elements, and in which:

FIGS. 1a and b illustrate the environment operational of an aperature synthesized radiometer made in accordance with the present invention and employed in a space platform orbiting the earth;

DETAILED DESCRIPTION

Figures 1A, 1B:
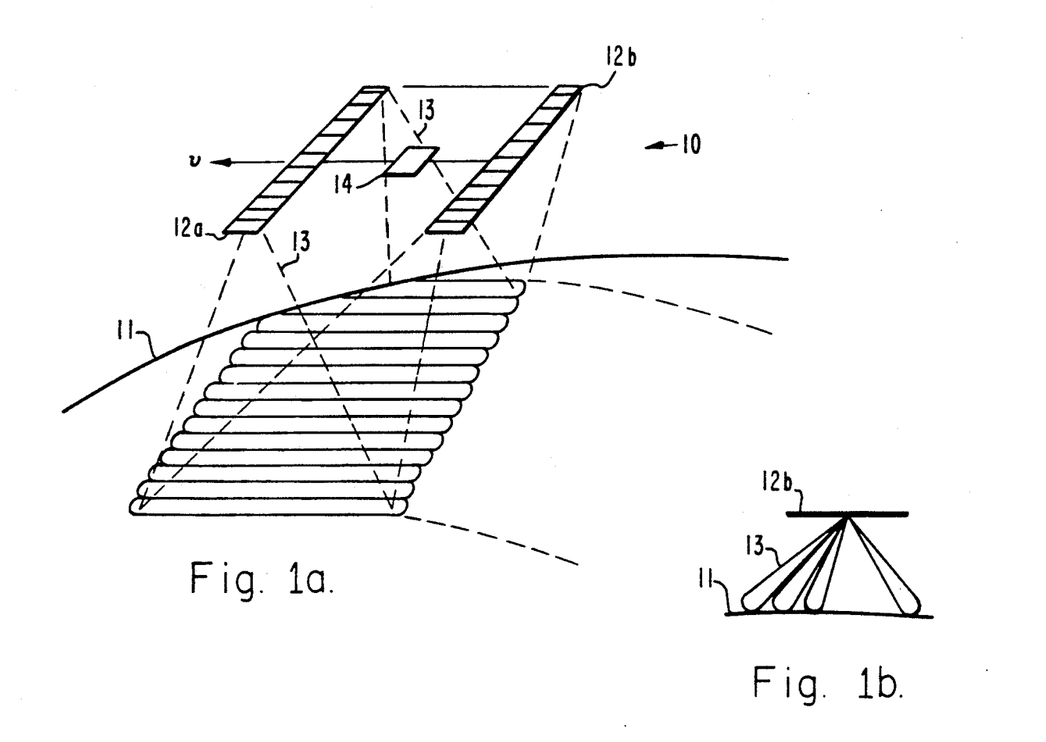

Referring to FIG. 1, an aperture synthesized radiometer 10 in accordance with the present invention and employed in an operational environment of a space platform orbiting the earth 11 is shown. The aperture synthesized radiometer 10 comprises two linear active receiving antennas 12a, 12b, each of which comprise linear array antennas. An imaging processor 14 comprises a digital beamforming processor which operates as the central imaging processing unit of the radiometer 10, a digital correlating interferometer and a matched filter, all of which will be discussed in detail hereinbelow.

The antennas 12 generate fanbeams 13 that provide for cross track resolution of the scene, since the antennas 12 are oriented transverse to the direction of travel (v) of the space platform relative to the earth. Along track resolution is provided by the interferometer and matched filter combination.

Figure 2:
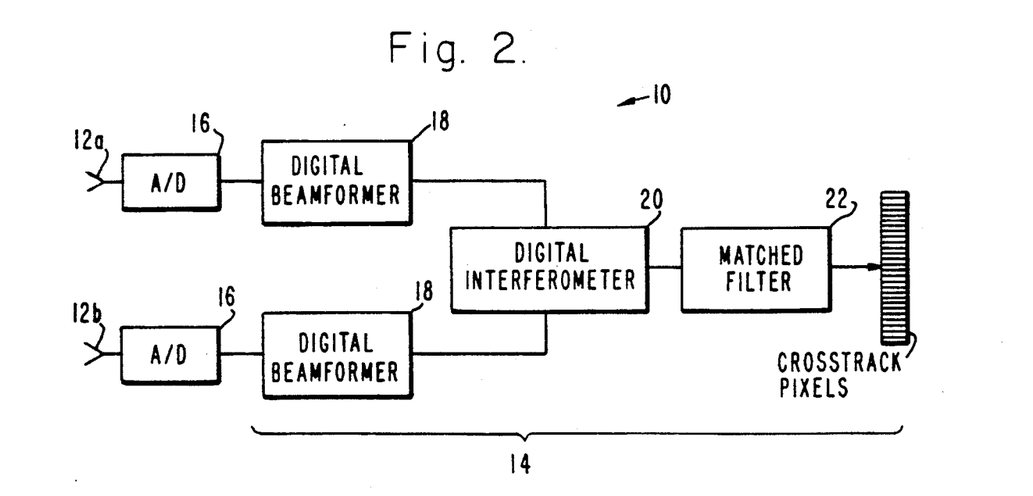
FIG. 2 illustrates a block diagram of an aperture synthesized radiometer in accordance with the present invention.

Referring to FIG. 2, a block diagram of the synthetic aperture radiometer 10 of the present invention is shown. The two linear active receiving antennas 12a, 12b are coupled by way of separate analog to digital converters 16 to the imaging processor 14. The imaging processor 14 includes two digital beamforming processors 18 whose outputs are coupled to a digital correlating interferometer 20, and the output of the interferometer 20 is coupled to a matched filter 22 which provides the digital output image of the radiometer 10, in the form of cross track pixels.

Figure 3:
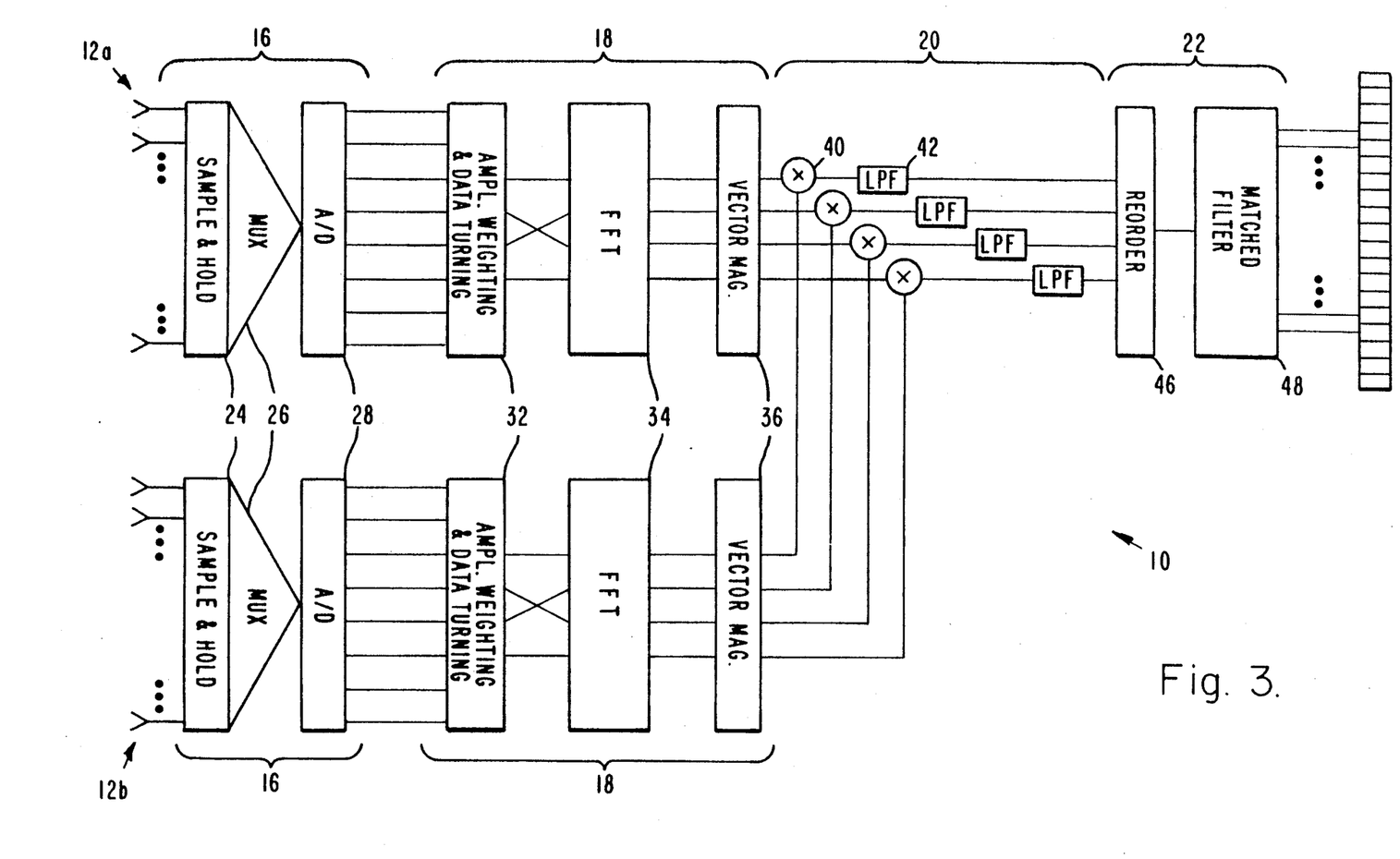
FIG. 3 illustrates a more detailed diagram of the aperture synthesized radiometer of FIG. 2.

FIG. 3 provides a more detailed diagram of the radiometer 10. As shown therein, the antenna elements of each antenna 12 are coupled by way of a sample and hold circuit 24 and an analog multiplexer 26 to an analog to digital converter circuit 28. The analog to digital converter circuit 28 provides a parallel set of outputs to each digital beamforming processor 18.

Each digital beamforming processor 18 comprises an amplitude weighting and data turning circuit 32. The amplitude weighting and data turning circuit is coupled to a digital Fourier transform circuit 34 which embodies a fast Fourier transform algorithm in hardware form. The digital Fourier transform circuit 34 is adapted to perform a 128 point fast Fourier transform of the data received thereby. Each fast Fourier transform circuit 34 is coupled to a vector magnitude circuit 36 which is adapted to adjust the magnitudes of the output signals from each digital beamforming processor 18. The outputs of the digital beamforming processor 18 are the received signal from 128 contiguous parallel fanbeams having their major axes parallel to the direction of the space platform.

Each digital correlating interferometer 20 is comprised of four two-input multipliers 40 and four low pass filters 42. Respective outputs from each digital beamforming processor 18 are coupled to respective first and second inputs of the multipliers 40 and the outputs of each multiplier 40 are coupled to the low pass filters 42. The matched filter 22 comprises a reordering circuit 46 whose inputs are coupled to the outputs of the digital correlating interferometer 20 whose output is coupled to a matched filtering circuit 48. Outputs of the matched filtering circuit 48 comprise imaging signals which represent the scene.

The operation of the aperture synthesized radiometer is as follows. The application described herein will be that of detecting and imaging soil moisture levels as viewed from a space platform orbiting the earth at an altitude of about 500 kilometers and having a relative velocity with respect to the ground. For soil moisture measurement, the antennas 12 are designed to operate at a frequency of 1.4 gigahertz with a 20 megahertz bandwidth.

In order to achieve a spatial resolution of about 5 kilometers by 5 kilometers, the two antenna arrays 12 each have an array length of 30 meters and a spacing of 30 meters. Each array comprises 256 active receiving elements. The two arrays form about 128 simultaneous fanbeams.

The imaging processor 14 synthesizes data collected by the antenna arrays 12 and displays an image of the soil moisture levels. In order to accomplish this, the digital beamforming processor 18 achieves two dimensional ground resolution using its multiple fanbeam beamforming utilizing fast Fourier transforms and interferometric capabilities with matched filtering.

Cross track resolution of the ground perpendicular to the direction of travel of the radiometer 10 is analyzed by means of the multiple fanbeams. By taking the Fourier transform of the signals collected by the individual antenna arrays 12, an image of each point in the field of view is obtained. This is accomplished by means of the fast Fourier transform circuit 34 which resolves a cross-track strip of ground into a line of patches (see FIG. 1). The digital transform of each fanbeam 13 represents each elongated patch of ground in the field of view. The 128 point fast Fourier transform circuit 34 is employed to achieve this cross track resolution.

In order to accomplish along track resolution of the scene, the two antenna arrays 12 are employed as a correlating interferometer for each fanbeam pair. Each antenna array 12, since it is physically separated from the other, receives radiation from a particular point on the earth from a different angle. As such the energy from each point follows a different path to each antenna array. Correlating (multiplying) the outputs of the two antenna arrays 12 cause the two fanbeams to interfere with each other. The movement of the radiometer platform relative to the ground causes the angle of arrival of the energy to vary, which varies the phase of the output waveform of the correlating interferometer 20.

The phase variation with respect to the angle of arrival of the energy is the instantaneous spatial frequency of the scene at any point. The interferometer 20 detects a modulated source frequency as it passes over any particular source point. Therefore, the motion of the radiometer 10 relative to the ground causes the interferometer 20 to see an apparent source frequency modulation, commonly known a chirp waveform. For successive point sources within each fanbeam 13, the interferometer 20 produces a corresponding lobe history. The sum of these lobe histories provides along track image resolution, since the interferometer 20 partitions each of the fanbeams in the perpendicular direction. The output of the correlating interferometer 20 is a "scrambled" image within the fanbeam. The order, or sequence, of the scrambling is the slowly varying chirp waveform which is determined by the separation of the antenna arrays 12 and relative motion of the space platform with respect to the earth.

Having accomplished both cross track and along track resolution of the scene, a complete resolution cell in formed by "descrambling" the output of the interferometer 20 by means of the matched filter 22. This collapses each chirp waveform to a point. The collection of these points are a line image of the scene, which may be displayed in a conventional manner on a monitor of choice.

Hence, in summary, the present invention forms image cells by creating fanbeams 13 by means of the digital beamformers 18 which provide simultaneous multiple fanbeams for crosstrack resolution. The fanbeams are correlated by the interferometer 20 and matched filter 22. The interferometer output signal for each fanbeam 13 is the sum of the lobe histories for each point in the fanbeam 13. The matched filter 22 collapses the interferometer output signals into an image of the scene to provide along track resolution.

With reference to FIG. 3, a more detailed description of the construction and operation of each of the major components of the radiometer 10 will be described. Each element of each antenna array 12 is coupled to inputs of the sample and hold circuit 24 whose outputs are coupled to the analog multiplexer 26. The multiplexer 26 is adapted to convert the parallel sets of signals into corresponding serial groups of signals. The use of this type of multiplexer increases the data rate while drastically reducing the number of interconnections required for the radiometer 10.

The analog to digital converter circuit 28 is an I, Q type converter which samples 256 input signals at a 20 megahertz rate at its input. The multiplexer 26 converts the 256 parallel I, Q pair samples into 8 groups of 32 parallel I, Q samples at 640 megahertz which are provided as serial output signals from the converter circuit 28.

Figure 4:
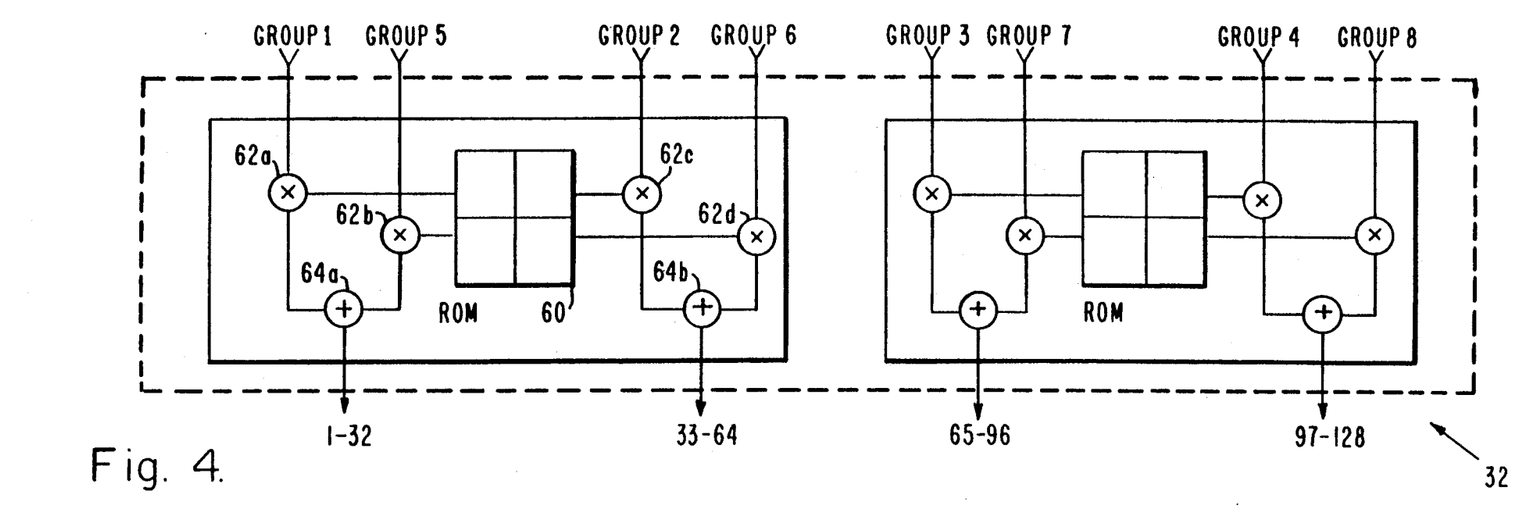
FIG. 4 illustrates the amplitude weighting and data turning portion of the aperture synthesized radiometer of FIG. 3.

FIG. 4 illustrates the amplitude weighting and data turning architecture employed in the radiometer 10. The details of construction are clearly shown in the figure and will not be discussed in detail. Generally, however, time invariant weights are stored in a 32×24 bit read only memory 60. A plurality of multipliers 62 provide for weighting of the signals while a plurality of adders 64 implement the data turning. The I, Q signals are provided to an amplitude weighting and data turning circuit 32 as 8 parallel groups of signals. The first and fifth groups, second and sixth groups, third and seventh groups and the fourth and eighth groups are weighted and summed. Consequently, four sets of I, Q signals are provided, with each sample being an 8 bit value.

The amplitude weighting is performed by the multipliers 62 which multiply each of the sampled signals by a predetermined weight, such as Chebyshev weights, or the like. This reduces the sidelobe levels contained in the fanbeams 13. However, such amplitude weighting causes undesirable mainlobe widening, which causes adjacent mainlobes to overlap at the fast Fourier transform filter output. To alleviate this problem, the data turning circuit 64 implements a 2:1 data turning of the signals which splits the 256 I, Q input signals into two halves and then sums the two halves together, yielding 128 I, Q samples, thus eliminating alternate lobes from the signals subsequently processed. The results of performing a 128 point fast Fourier transform on these 128 samples is equivalent to disposing of every other mainlobe produced by a 256 point fast Fourier transform on the original 256 input signals.

Without amplitude weighting, all samples are of equal amplitude in the time domain and when they are converted to the frequency domain by the fast Fourier transform circuit 34 they have a main lobe and a plurality of side lobes having a 6 dB octave, for example. However, when utilizing the amplitude weighting, the samples have a triangularly shaped amplitude configuration in the time domain and when they are converted to the frequency domain they have a main lobe and a plurality of amplitude reduced side lobes having an 18 dB octave, for example. The data turning in essence narrows and increases the amplitude of the main lobe to eliminate mainlobe overlap.

Figure 5:
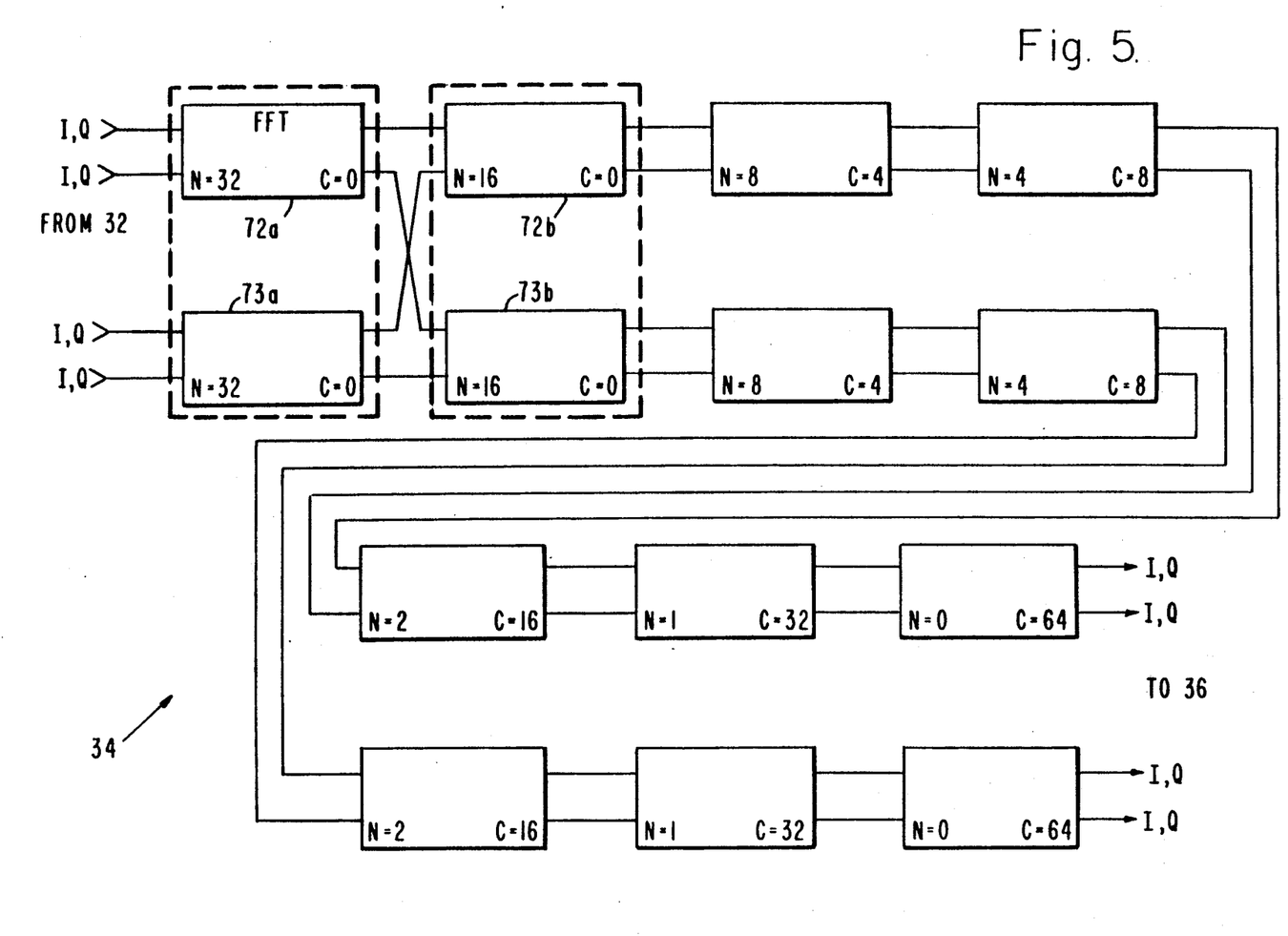
FIG. 5 illustrates the fast Fourier transform circuit of the aperture synthesized radiometer of FIG. 3 which forms multiple simultaneous fanbeams.

FIG. 5 shows a detailed diagram of the fast Fourier transform circuit 34 of the beamformer 18. This circuit includes two parallel sets of fast Fourier transform circuits 72, 73, which comprise butterfly cells, and which implement butterfly computations. The outputs of the first butterfly cell of each parallel set is cross coupled to an input of the second butterfly cell of the alternate set. The balance of the cells are serially coupled together as shown in the figure. A total of seven butterfly computations are performed in this implementation.

Figure 6:
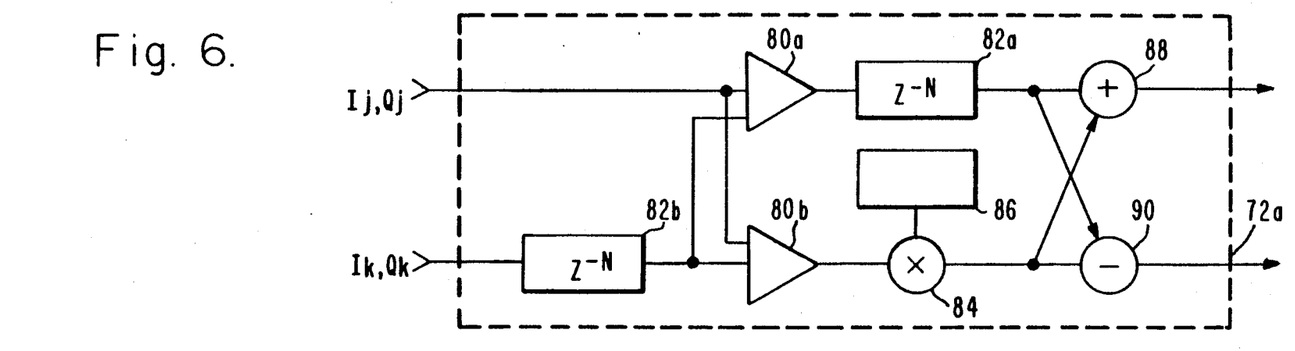
FIG. 6 illustrates the fast Fourier transform butterfly architecture employed in the fast Fourier transform circuit of FIG. 5.

As shown, this configuration implements a decimation-in-time algorithm. This fast Fourier transform circuit 34 comprises two sets of seven butterfly cells that are cascaded. The two sets work in parallel with the exception of the signal exchange between the first an second cell 72a, 73b and 73a, 72b. The specifics of the butterfly architecture are shown in FIG. 6. Each I, Q input signal is coupled to a separate multiplexer 80a, 80b, with one signal passing through a delay 82b prior to the multiplexer 80b. The output of the undelayed multiplexer 80a is then delayed in a second delay 82b, while the second output is coupled through a two-input multiplier 84 which couples adjustment factors from a read only memory 86 to the signals processed along that path. The output signals of each channel are cross coupled and sum and difference signals are generated from adders 88, 90 as the output signals of the butterfly cell 72a.

The fast Fourier transform circuit 34 generates 128 I, Q fanbeam values serially over its four output channels. The output signals, however, emerge in a bit reversed order, and consequently the fanbeam values are also in reversed order. In order to correct the ordering problem introduced by the transform architecture, a reordering section is provided just prior to the matched filter, which rearranges the bit reversed outputs back into normal order. This section will be discussed in detail at a later point.

Figure 7:
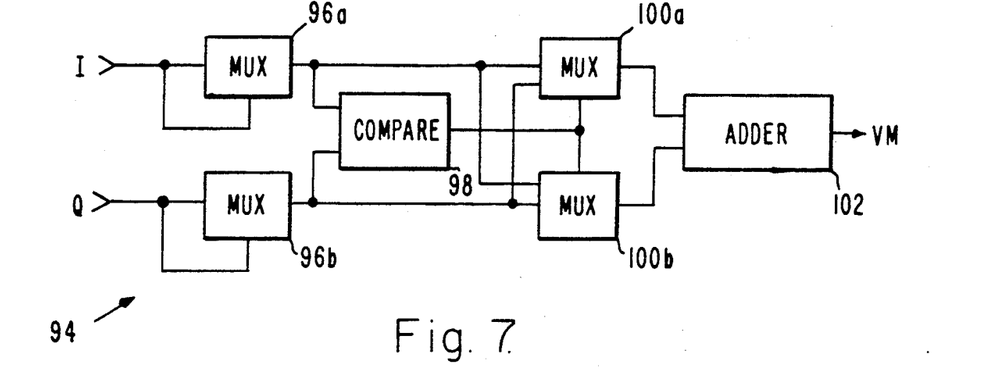
FIG. 7 illustrates the vector magnitude portion of the aperture synthesized radiometer of FIG. 3.

The vector magnitude circuit 36 of the beamformer 18 is shown in detail in FIG. 7. The vector magnitude circuit 36 comprises four parallel cells each of which comprise the cell logic 94 shown in FIG. 7. This cell logic 94 shown in FIG. 7 comprises two two-input multiplexers 96a, 96b which accept I and Q input signals and route these signals to a comparison circuit 98. The I and Q signals are then applied to a second set of cross coupled multiplexers 100 controlled by the output of the comparison circuit 98 and then applied to an adder 102. The adder 102 adds the input signals and provides an output signal comprising the magnitude of the signal being processed.

Figure 8:
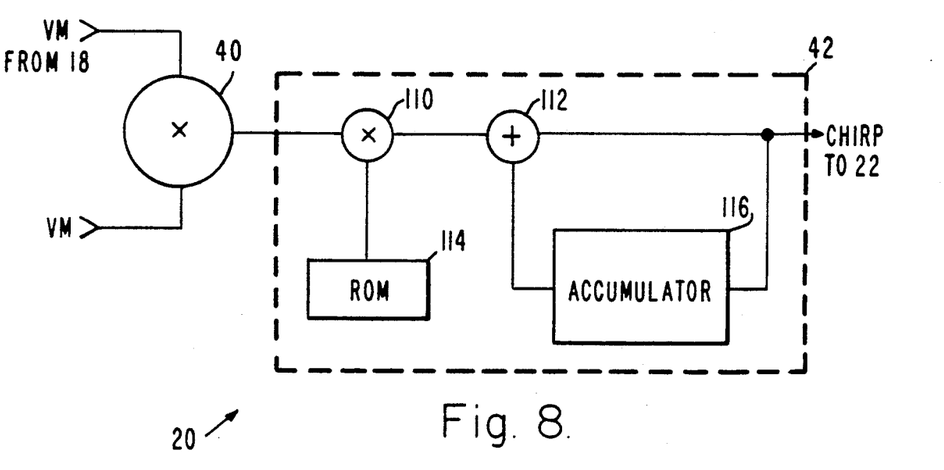
FIG. 8 illustrates the architecture for the digital correlating interferometer circuit of the aperture synthesized radiometer of FIG. 3.

The interferometer 20 shown in FIG. 3 includes four parallel channels comprising a multiplier 40 and a low pass filter 42. The details of the low pass filter 42 are also shown in FIG. 8. The low pass filter 42 comprises a two-input multiplier 110 employed to multiply the signal values by predetermined values stored in a read only memory 114. The output of the two input multiplier 110 is coupled to an adder 112 which has an accumulator 116 coupled in a feedback arrangement from its output to its input. The accumulator 116 comprises a 32×10 register file.

The low pass filter 42 stores 32 signals received from the frist multiplier 40 before the next 32 signals are added to them. The low pass filter 42 is a finite impulse response (FIR) filter implemented by input weighting and accumulation. The output signal from the interferometer 20 comprises chirp signals in which the output comprises 32 consecutive chirp waveforms which appear in bursts.

The matched filter 22 of the radiometer 10 comprises the reordering circuit 46 discussed above along with the matched filter circuit 48. The filter is matched to detect the specific chirp waveforms which collapses the processed signals to a series of points which represent the scene. This is accomplished in a conventional manner as is well-known in the art.

The above description has detailed the design, construction and operation of a aperture synthesized radiometer employing digital beamforming and interferometry which is capable of imaging and displaying microwave energy emitted or reflected by earth surface features. In addition, the present invention also contemplates a method of digitally processing an image to provide an image of the scene. This technique provides multiple fanbeams simultaneously and in a cost effective manner. As a result, more integration time, a factor of 128, is available, and hence better sensitivity is provided.

One method in accordance with the present invention comprises the steps of receiving radiation emitted or reflected from an scene by means of a plurality of substantially parallel antenna arrays. The next step involves converting received radiation into corresponding digitized signals by means of an analog to digital converter coupled to the plurality of antenna arrays. Finally the method provides for processing and digitally synthesizing a large aperture to provide an image corresponding to the scene by means of a digital beamformer and correlating interferometer and matched filter coupled to the analog to digital converter.

The synthesizing step generally comprises processing the digitized signals by means of individual digital beamformers coupled to two antenna arrays. A set of fanbeam signals are generated for each antenna array in order to provide crosstrack imaging of the scene. The sets of fanbeam signals provided by each of the beamformers are then processed by means of a digital interferometer to correlate corresponding pairs of fanbeam signals from the two sets of fanbeam signals. This process step generates a chirp signal for each pair of fanbeam signals. The chirp signals are then processed by means of a matched filter coupled to the digital interferometer to transform each chirp signal into a corresponding image point of the scene, thus providing along track imaging of the scene.

Numerous other methods are clearly derivable from a reading of the specification herein and will not be discussed in any specific detial. These methods are presented in the claims section of this document.

Thus, there has been described an aperture synthesized radiometer and method of processing image data which provides for the detection and imaging of soil moisture in the atmosphere and on the earths surface from a remotely located imaging system. The present invention is not, however, limited to the detection and display of moisture levels emanating from the earth and atmosphere. There are numerous other applications of the present invention including the determination of ocean temperature, and roughness of sea surface, and the like.

Consequently, it is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. An aperture synthesized radiometer comprising:
two substantially parallel linear antenna arrays adapted to receive radiation emitted or reflected from a scene and adapted to generate two sets of substantially parallel fanbeams;
analog to digital conversion means coupled to the two antenna arrays for converting received radiation into corresponding digitized radiation signals; and
digital beamforming means substantially colocated with the antenna arrays and the analog to digital conversion means for processing and synthesizing the digitized radiation signals to provide an image corresponding to the scene, said digital beamforming means comprising means for digitally forming a plurality of cross track fanbeams and means for cross-correlating the plurality of digitally formed cross track fanbeams to produce an image of the scene.

2. The aperture synthesized radiometer of claim 1 wherein said digital beamforming means comprises:

individual digital beamforming means coupled to each of the antenna arrays for generating a set of fanbeam signals for each antenna array in order to provide cross track imaging of the scene;

digital interferometer means coupled to the individual beamforming means for digitally processing the sets of fanbeam signals provided by each of the digital beamforming means to correlate corresponding pairs of fanbeam signals from the two sets of fanbeam signals to produce a chirp signal for each pair of fanbeam signals in order to provide along track imaging of the scene; and matched filter means coupled to the digital interferometer means for processing the chirp signals to transform each chirp signal into a corresponding image point in the scene.

3. The aperture synthesized radiometer of claim 2 wherein each of said individual digital beamforming means each comprises fast Fourier transform means for transforming the digitized radiation signals into the fanbeam signals.

4. The aperture synthesized radiometer of claim 3 wherein each of said individual digital beamforming means further comprises:

amplitude weighting means for providing amplitude weighting of the digitized radiation signals to reduce fanbeam signal sidelobe levels; and data turning means coupled to the amplitude weighting means for eliminating alternate mainlobes from the digitized radiation signals to reduce mainlobe widening of the digitized radiation signals.

5. The aperture synthesized radiometer of claim 3 wherein each of said fast Fourier transform means comprising a decimation-in-time algorithm implemented by means of a plurality of parallel and cascaded butterfly computation means.

6. The aperture synthesized radiometer of claim 5 which further comprises reordering means coupled to the fast Fourier transform means for reversing the order of the fanbeam signals provided thereby.

7. The aperture synthesized radiometer of claim 1 wherein said analog to digital conversion means comprises;

a plurality of sample and hold circuits for sampling a plurality of predetermined groups of signals from the received radiation signals;

a plurality of analog multiplexers coupled to respective ones of the sample and hold circuits for converting the groups of parallel radiation signals into corresponding serial groups of radiation signals; and a plurality of analog to digital converters coupled to respective ones of the plurality of analog multiplexers for converting the serial groups of analog radiation signals into corresponding digital signals.

8. The aperture synthesized radiometer of claim 2 wherein said digital interferometer means comprises:

a plurality of multipliers coupled to corresponding outputs of each of the individual beamforming means for multiplying the respective signals received thereby; and a plurality of low pass filters coupled to respective ones of the plurality of multipliers.

9. The aperture synthesized radiometer of claim 8 wherein said low pass filter comprises:

a finite impulse response low pass filter comprising a second multiplier, including a read only memory which stores weighting coefficients, coupled to a predetermined set of the multipliers;

an adder coupled to the multiplier, and an accumulator coupled from the output of the adder to one of its inputs.

10. A method of digitally processing an image comprising the steps of:

receiving radiation emitted or reflected from a scene by means of two substantially parallel antenna arrays and generating two sets of substantially parallel fanbeams;

converting received radiation into corresponding digitized radiation signals; and processing and synthesizing the digitized radiation signals to provide an image corresponding to the scene, by digitally forming a plurality of cross track fanbeams and cross-correlating the plurality of digitally formed cross track fanbeams to produce an image of the scene.

11. The method of claim 10 wherein the processing and synthesizing step comprises:

generating a set of fanbeam signals for each antenna array in order to provide crosstrack imaging of the scene;

processing the sets of fanbeam signals to correlate corresponding pairs of fanbeam signals from the two sets of fanbeam signals;

generating a chirp signal for each pair of fanbeam signals in order to provide along track imaging of the scene; and matched filtering the chirp signals to transform each chirp signal into a corresponding image point in the scene.

12. The method of claim 11 wherein the step of processing and synthesizing the digitized signals comprises the step of:

fast Fourier transforming the digitized radiation signals to transform the digitized radiation signals into the fanbeam signals.

13. The method of claim 12 wherein the step of processing and synthesizing the digitized radiation signals further comprises the steps of:

amplitude weighting the digitized signals to reduce fanbeam signal sidelobe levels; and data turning the amplitude weighted signals to eliminate alternate mainlobes from the digitized radiation signals to reduce mainlobe widening of the digitized radiation signals.

14. The method of claim 13 wherein the step of processing and synthesizing the digitized signals further comprises the step of:

processing and synthesizing the digitized radiation signals by means of a decimation-in-time algorithm.

15. The method of claim 13 wherein the step of processing and synthesizing the digitized radiation signals further comprises the step of:

reversing the order of the fanbeam signals provided by the fast Fourier transform step.

16. The method of claim 10 wherein said converting step comprises:

sampling a plurality of predetermined groups of signals from the received radiation signals;

converting the groups of parallel radiation signals into corresponding serial groups of radiation signals; and converting the serial groups of analog radiation signals into corresponding digital signals.

17. The method of claim 11 wherein processing the sets of fanbeam signals comprises the steps of:
multiplying the respective signals by a plurality of multipliers; and
low pass filtering the multiplied signals.

18. A method of digitally processing an image comprising the steps of:
receiving radiation emitted or reflected from a scene by means of two substantially parallel antenna arrays and generating two sets of substantially parallel fanbeams;
converting received radiation into corresponding digitized radiation signals by means of an analog to digital conversion means coupled to the two antenna arrays;
processing and synthesizing the digitized radiation signals to provide an image corresponding to the scene by means of digital beamforming means coupled to the analog to digital conversion means by digitally forming a plurality of cross track fanbeams and cross-correlating the plurality of digitally formed cross track fanbeams to produce an image of the scene; and
transmitting the image to a remote location for viewing.

19. The method of claim 18 wherein the processing and synthesizing step comprises:
generating a set of fanbeam signals for each antenna array in order to provide crosstrack imaging of the scene;
processing the sets of fanbeam signals provided by each of the beamforming means by means of digital interferometer means coupled to the individual beamforming means to correlate corresponding pairs of fanbeam signals from the two sets of fanbeam signals;
generating a chirp signal for each pair of fanbeam signals in order to provide along track imaging of the scene; and
processing the chirp signals by means of matched filter means coupled to the digital interferometer means to transform each chirp signal into a corresponding image point in the scene.

20. The method of claim 19 wherein the step of processing and synthesizing the digitized radiation signals comprises the step of:
processing the digitized radiation signals by means fast Fourier transform means to transforming the digitized signals into the fanbeam signals.

21. The method of claim 20 wherein the step of processing and synthesizing the digitized radiation signals further comprises the steps of:
amplitude weighting the digitized radiation signals to reduce fanbeam signal sidelobe levels; and
data turning the amplitude weighted signals to eliminate alternate mainlobes from the digitized radiation signals to reduce mainlobe widening of the digitized radiation signals.

22. The method of claim 21 wherein the step of processing and synthesizing the digitized radiation signals further comprises the step of:
processing and synthesizing the digitized radiation signals by means of a decimation-in-time algorithm implemented by means of a plurality of parallel and cascaded butterfly computation means.

23. The method of claim 22 wherein the step of processing and synthesizing the digitized radiation signals further comprises the step of:
reversing the order of the fanbeam signals provided by the fast Fourier transform means.

24. The method of claim 18 wherein said converting step comprises:
sampling a plurality of predetermined groups of signals from the received radiation signals by means of a plurality of sample and hold circuits;
converting the groups of parallel signals into corresponding serial groups of signals by means of a plurality of analog multiplexers coupled to respective ones of the sample and hold circuits; and
converting the serial groups of analog radiation signals into corresponding digital signals by means of a plurality of analog to digital converters coupled to respective ones of the plurality of analog multiplexers.

25. The method of claim 19 wherein processing the sets of fanbeam signals provided by each of the beamforming means by means of digital interferometer means comprises the steps of:
multiplying the respective signals received there by means of a plurality of multipliers coupled to corresponding outputs of each of the individual beamforming means; and
processing the multiplied signals by means of a plurality of low pass filters coupled to respective ones of the plurality of multipliers.

26. An aperture synthesized radiometer comprising:
two substantially parallel linear antenna arrays adapted to receive radiation emitted or reflected from a scene and adapted to generate two sets of substantially parallel fanbeams;
analog to digital conversion means coupled to the two antenna arrays for converting received radiation into corresponding digitized radiation signals; and
digital beamforming means substantially colocated with the antenna arrays and the analog to digital conversion means for processing and synthesizing the digitized radiation signals to provide an image corresponding to the scene, said digital beamforming means comprising means for digitally forming a plurality of cross track fanbeams and means for cross-correlating the plurality of digitally formed cross track fanbeams to produce an image of the scene.

27. The aperture synthesized radiometer of claim 26 wherein said digital beamforming means comprises:
individual digital beamforming means coupled to each of the antenna arrays for generating a set of fanbeam signals for each antenna array in order to provide cross track imaging of the scene;
digital interferometer means coupled to the individual beamforming means for digitally processing the sets of fanbeam signals provided by each of the digital beamforming means to correlate corresponding pairs of fanbeam signals from the two sets of fanbeam signals to produce a chirp signal for each pair of fanbeam signals in order to provide along track imaging of the scene; and
matched filter means coupled to the digital interferometer means for processing the chirp signals to transform each chirp signal into a corresponding image point in the scene.

* * * * *